(12) United States Patent
Tatarek

(10) Patent No.: US 6,189,531 B1
(45) Date of Patent: Feb. 20, 2001

(54) ADJUSTABLE FLOW REGULATOR DEVICE

(75) Inventor: Andrew Richard Thomas Tatarek, Aldershot (GB)

(73) Assignee: Protector Technologies BV, Schiedam (NL)

( * ) Notice: Under 35 U.S.C. 154(b), the term of this patent shall be extended for 0 days.

(21) Appl. No.: 09/043,838

(22) PCT Filed: Oct. 4, 1996

(86) PCT No.: PCT/GB96/02436
§ 371 Date: Mar. 27, 1998
§ 102(e) Date: Mar. 27, 1998

(87) PCT Pub. No.: WO97/13185
PCT Pub. Date: Apr. 10, 1997

(30) Foreign Application Priority Data

Oct. 4, 1995 (GB) .................................. 9520221

(51) Int. Cl.[7] .............. A62B 9/02; A62B 7/00; A61M 15/08; G05D 7/00
(52) U.S. Cl. ............... 128/205.24; 128/205.11; 128/203.24; 137/102
(58) Field of Search ............. 128/203.24, 204.25, 128/204.18, 205.24, 205.11; 137/102

(56) References Cited

U.S. PATENT DOCUMENTS

| | | | |
|---|---|---|---|
| 4,008,716 | * 2/1977 | Amlong | 128/205.24 |
| 4,022,202 | 5/1977 | Price | 128/145.8 |
| 4,401,116 | 8/1983 | Fry et al. | 128/205.24 |
| 5,348,001 | * 9/1994 | Danon | 128/205.24 |
| 5,619,988 | * 4/1997 | Mattila et al. | 128/205.24 |
| 5,755,220 | * 5/1998 | Ando | 128/205.24 |
| 5,950,623 | * 9/1999 | Michell | 128/205.24 |

FOREIGN PATENT DOCUMENTS 2174609  11/1986  (GB) ........................... A61M/16/00

* cited by examiner

Primary Examiner—John G. Weiss
Assistant Examiner—Todd M. Martin
(74) Attorney, Agent, or Firm—Volpe and Koenig, P.C.

(57) ABSTRACT

An adjustable gas flow regulator device primarily for use in medical care, said device comprising a two-part body (8/25) having a high pressure gas inlet connector (1) and a gas outlet connector (16) mounted thereon. Mounted within the body is a conventional regulator comprising a piston (9) axially movable in a stepped bore (46/47). Mounted between the output of the regulator and the outer connector (16) is a flow selector device comprising a flow selecting member (13) rotatable by means of a knob (31). The flow selecting member (13) is formed with a plurality of radially extending bores (54) in the outer part of each of which is fitted a setting plug which may be externally adjustable by a tool (not shown). The inner part of each bore forms part of the route by which gas passes to the outer connector and the flow of gas through each such inner part can thus be adjusted by means of the setting plug so that, at each respective angular position of knob (31), a different flow setting can be obtained, as necessary.

20 Claims, 2 Drawing Sheets

ADJUSTABLE FLOW REGULATOR DEVICE

BACKGROUND

This invention relates to an adjustable gas flow regulator device.

There is a requirement in medical care for an adjustable flow regulator which is able to administer ranges of preset flows of typically 0.1 to 15 L/M of oxygen to patients either in care or in the home. The regulator device of the present invention is intended to meet this need as well as being useful in a broad range of applications where an adjustable gas flow is required.

SUMMARY

According to the invention there is provided an adjustable flow regulator device comprising a body, an inlet connector and an outlet connector mounted on said body, regulator means within said body operable to receive gas from said inlet connector and provide a regulated supply, and adjustable flow selector means within said body operable to receive gas from said regulator means and provide an adjustable flow to said outlet connector, said regulator device being characterised in that said flow selector means comprises a passage through which gas flows from said regulator means to said outlet connector and a setting plug adjustably mounted to selectively restrict the passage of gas through said passage, said setting plug having engagement means by which it may be engaged with an externally applied setting tool for adjustment of said plug to obtain the desired gas flow rate through said passage.

In an embodiment of the invention, said setting plug is mounted in a bore formed in a wall of said passage and is movable along said bore so as to protrude into said passage by an adjustable amount to thereby enable the flow through said passage to be adjusted. The plug may be a ready sliding fit in said passage, means being provided for locking the plug in position once set at the desired position by said external tool. Alternatively the plug may be screw threaded within said bore in such a way that said setting tool engages the plug so as to rotate the plug and thereby adjust its setting. A special locking threaded plug may be used, or separate means may be provided for locking the threaded plug in position once set. In the preferred embodiment, the plug is sized so as to be a tight sliding, for example interference, fit in said bore so that, once set, the plug maintains its position in the bore.

In order to enable adjustment by the setting tool, it is preferred that the bore is a through bore and can be brought into alignment with a setting hole in the body through which said setting tool can be applied from the exterior in order to adjust the plug.

To provide for an adjustable flow rate through the valve, the flow selector means preferably further comprises a movable flow selecting member in which is formed a plurality of said passages each having an associated setting plug. Means are further provided for adjusting the position of said flow selecting member in discrete steps at each of which at least one of said passages is in fluid communication with said outlet connector, the remaining passage or passages being blocked. Thus by adjusting the setting plug for each passage to a different gas flow setting, the output gas flow rate can be made adjustable by changing the position of the flow selecting member.

In a preferred embodiment of the invention the flow selecting member is rotatably mounted within said body and is rotated by means of an externally mounted manually adjustable knob. Means are provided for locating said flow selecting member at a plurality of predetermined angular spaced positions, each corresponding to a position at which said at least one passage is in fluid communication with said outlet connector. A further angular position may be provided in which none of the passages are in fluid communication with said outlet connector, this corresponding to the "off" position of the regulator device.

Preferably just a single setting hole is provided in said body, the arrangement being such that, at each of the preset positions of the flow selecting member, at least one of the plug through bores is in alignment with the setting hole to permit adjustment of the flow rate at each position of the flow selecting member. In the case of a rotatably mounted flow selecting member, it is preferred that the plug through bores are oriented approximately radially with respect to the axis of rotation of the flow selecting member so that, as the flow selecting member is rotated to each of its preset angular positions, a different setting plug, having a different adjustment, is brought into alignment with the setting hole.

In the preferred embodiment the setting hole is formed underneath the outlet connector, which latter is detachable from the body, so as to hide the setting hole and thereby discourage tampering when in service. In addition a sealing cover may be fitted over the setting hole to seal the hole once the flow settings have been made. This cover may be a permanent or semi-permanent affair, but preferably it is removable to allow later readjustment of the flow settings, should this prove necessary. Where the setting hole is situated underneath the outlet connector, in the manner just described, the cover can be conveniently such that it is retained in place by the outlet connector, so that when the outlet connector is, removed, the cover can be readily removed to allow adjustment of the settings.

DETAILED DESCRIPTION OF THE PREFERRED EMBODIMENTS

In order that the invention may be better understood, an embodiment thereof will now be described by way of example only and with reference to the accompanying drawings.

Figure 1:
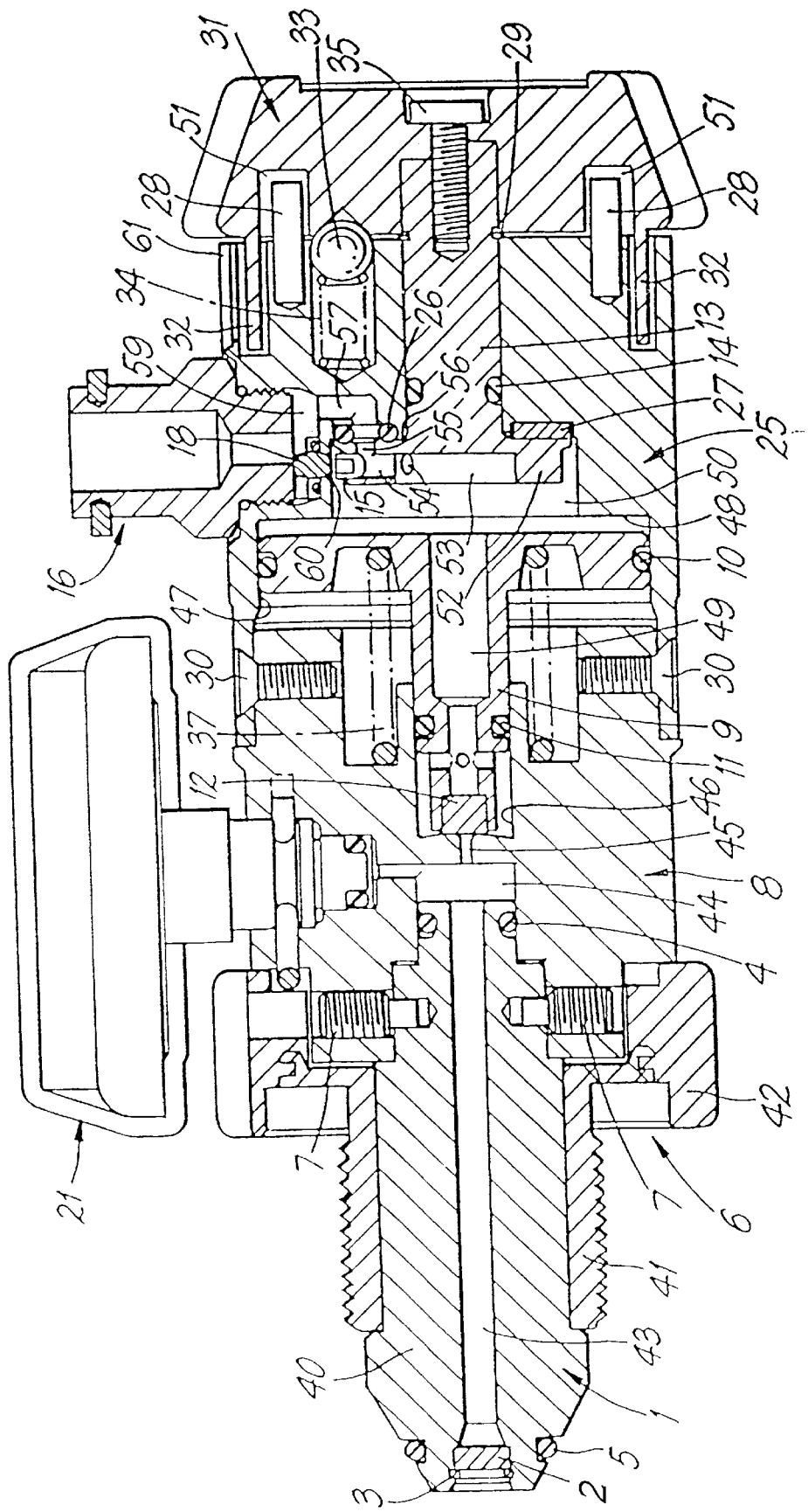
FIG. 1 is a diagram of an adjustable gas flow regulator device according to the invention.

Referring to FIG. 1 the regulator device comprises a generally cylindrical body formed in two parts: a high pressure inlet part 8 made of aluminium alloy and a low pressure outlet part 25 made of aluminium alloy or plastics material. The two body parts are attached to one another in axial alignment by means of radially spaced countersunk bolts 30. Mounted on the inlet body part 8 is an inlet gas connector 1 which provides a standard connection for high pressure gas. The particular connector shown is a bullnose connector to BS (British Standard) 341 type 3. The main body 40 of the connector is attached to the body part 8 by angularly spaced dog point grub screws 7 and sealing is effected by an O-ring 4, for example of rubber.

Rotatably mounted about the main body 40 is a collar 6 having a screw threaded portion 41 and a thumbwheel portion 42. Rotation of the thumbwheel enables the screw threaded portion 41 to be screw threaded to the corresponding gas supply connector (not shown), thus connecting the high pressure gas source to the inlet of the regulator. Sealing to the gas supply connector is effected by an O-ring 5.

Gas from the supply source enters the regulator via an axial bore 43 in the body 40 of the inlet connector 1. A disc filter 2 of sintered material retained by a clip 3 filters the incoming gas. The gas enters a high pressure chamber 44 in which the input gas pressure is monitored by a pressure gauge 21. The gas leaves the chamber 44 through a small jet 415 into the regulator itself.

The regulator comprises a generally cylindrical chamber comprising a first narrow bore section 46 formed in the body part 8 and a second wide bore section 47 formed in the body part 25. A piston 9 is axially mounted for sliding movement along said bores and is biassed to the right in the drawing by means of a spring 37. The piston 9, which is made for example of brass, is of stepped cylindrical construction, having a narrow portion adapted to be a sliding fit in the narrow bore section 46 and a relatively wider portion adapted to be a sliding fit in the wide bore section 47. Respective sealing O-rings 11 and 10 seal the narrow and wide portions of the piston within their respective bore sections. Leftwards movement of the piston 9 is limited by its engagement against the mouth of the jet 45. At the left hand end of the piston 9 is fitted a seat 12 of plastics material, for example nylon, which provides an effective seal to close off the jet 45. Rightwards movement of the piston 9 is limited by its engagement with a shoulder 48 formed in the body part 25.

Operation of the regulator is conventional and will be understood without detailed explanation by those skilled in the art. Gas emerging from the jet 45 enters the narrow bore section 46 and passes via four equally radially spaced passages into the hollow interior 49 of the piston 9. The gas emerges into a low pressure chamber 50 at the right hand side of the piston 9 and acts to move the piston to the left in opposition to the force of the spring 37. An equilibrium position is reached in which the pressure in chamber 50 is regulated at some value lower than the inlet pressure, dependent upon the spring force and other factors. Typically the rated inlet pressure will be in the range 13.5 Bar to 200 Bar; a typical outlet pressure is in the range 20 PSI to 25 PSI.

Rotatably mounted in an axial bore in the body part 25 is a flow selecting member 13 made, for example, of brass. The flow selecting member may be rotated by means of a flow selector knob 31 which is attached thereto by means of a retaining screw 35. The flow selecting member is arranged to locate into a plurality of discrete angularly spaced positions by means of one or more locking devices. Each such locking device comprises a spring 34 which biases a ball 33 into a detent formed in the undersurface of the selector knob 31. A non-continuous circular slot 51, centred on the axis, is formed in the undersurface of the selector knob 31 and acts to engage stop pins 28 fitted in blind bores in the body part 25. As the knob 31 is rotated, the ends of the slot 51 come into engagement with one of the pins 28, thus preventing further rotation in that direction. In practice, a plurality of angularly spaced blind bores may be formed to receive said stop pins 28, and the pins placed in only those bores which are necessary to obtain the desired extent of angular movement of the flow selecting member. This enables a single body part 25 to be used for regulator devices providing different numbers of flow settings. The knob 31 is formed with a skirt 32 which is visible through a window 61 formed in the body part 25 to enable the user to view the setting of the knob.

The left hand end of the flow selecting member 13 is formed with a flange 52 defining a shallow circular depression 53. Extending radially through the flange 52 are a plurality of angularly spaced through bores 54, of which two are visible in the drawing. Each of the bores 54 extends from the depression 53 at its inner end to the outer edge of the chamber 50 at its outer end. In addition a further bore 55 is formed in the flange 52 extending parallel with the axis from the respective bore 54 and opening into the rear face 56 of the flange 52.

The arrangement is such that, at all but one of the preselected angular positions of the flow selecting member 13, a respective one of the bores 55 is in alignment with a bore 57 in the body part 25. In one of the preselected angular positions, it is arranged that no bore 55 is in alignment with the bore 57, this corresponding to the "off" position of the device.

Sealing connections between the flow selecting member 13 and the body part 25 are provided for by respective O-ring seals 14 and 26. The seal 26 is located in an annular slot formed in that surface of the body part 25 which faces the rear surface 56 of flange 52. The seal 26 thus ensures sealing connected between the selected bore 55 in the flange 52, and the bore 57 in the body part 25.

Smooth friction-free rotation of the flow selecting member 13 is ensured by means of a plurality of angularly spaced pads 27 of low-friction material such as acetal which are located in slots on the body part 25. Longitudinal movement of the flow selecting member is prevented by a circlip 29. In normal operation of the device, the gas pressure within chamber 50 will act to push the flow selecting member 13 in a rightwards direction against the pads 27; the circlip 29 is thus intended primarily to prevent inwards movement of the flow selecting member 13 which might release the seal formed by O-ring 26.

The bore 57 in the body part 25 opens at its outlet end in an outlet chamber 59 which forms the lower end of a threaded bore in which is attached the outlet connector 16. In the embodiment shown, this takes the form of a standard low pressure bayonet connector, but it will be appreciated that other types are possible.

Thus it will be seen that gas at a low regulated pressure may pass from the chamber 50 through bores 54,55 and 57 in turn to the chamber 59 and thence exit via the outlet connector 16. The particular bores 54, 55 through which the gas passes can be selected by rotation of the knob 31.

Figure 2:
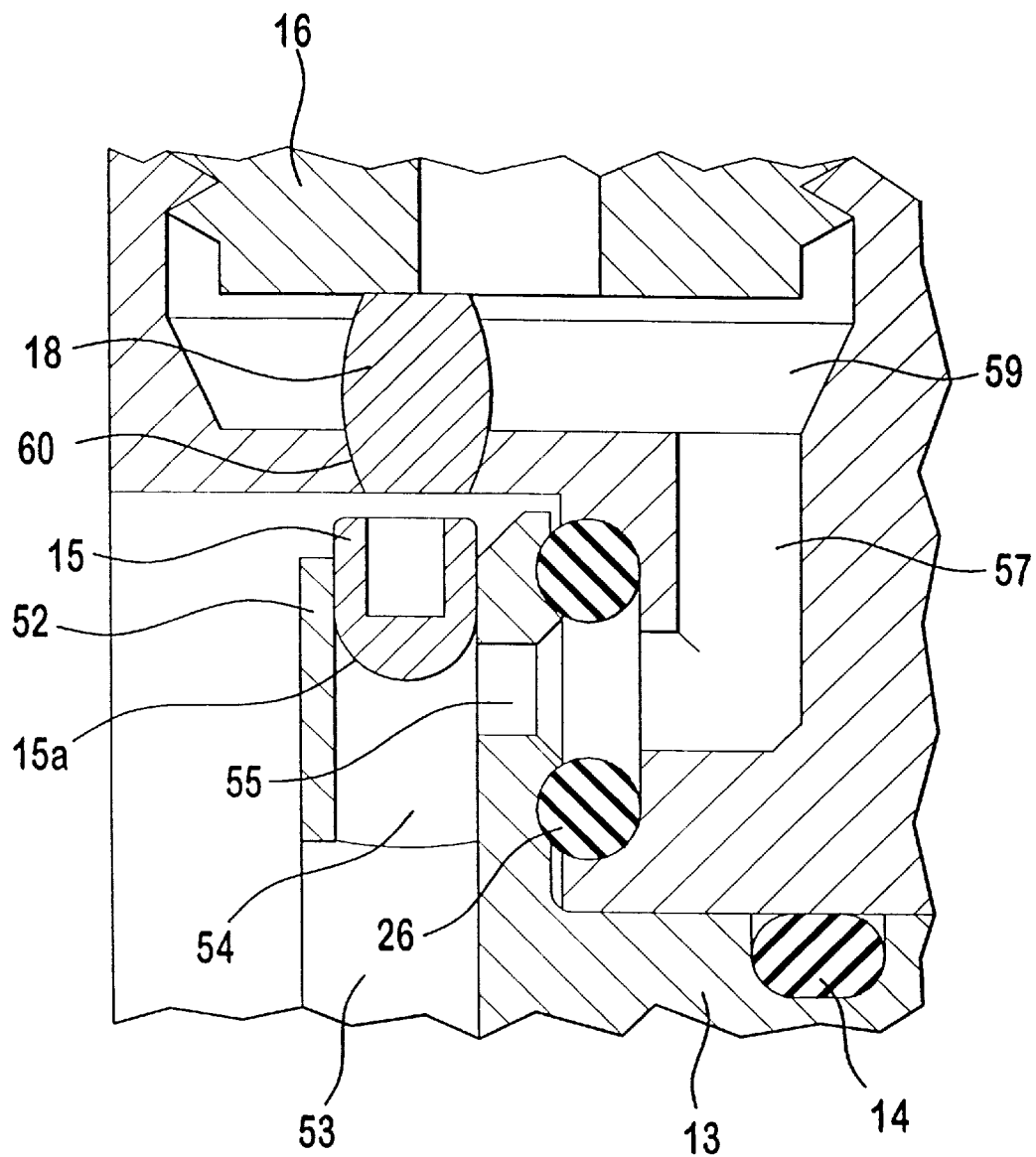
FIG. 2 is a diagram of the setting plug and bores according to the invention.

The flow adjustment arrangement illustrated in FIG. 2 will now be described. In the outer end of each bore 54, that is, in that end of the bore which is radially beyond the respective bore 55, is fitted a setting plug 15 made, for example, of brass. An end 15*a* of the plug 15 which faces into the bores 54/55 is of spherical shape to give a reasonably graduated reduction of flow as the plug is moved radially inwardly along the bore 54. Alternative end shapes could be considered, such as conical, but it is felt that some end shapes, such as a plain flat end, would give a sharp flow cut off, making it difficult to adjust the plug accurately for a desired flow rate.

The opposite (outer) end of the setting plug 15 is formed with a blind bore into which the end of a setting tool (not shown) can be inserted to allow adjustment of the plug. The bore is not essential, but is felt to be desirable to locate the setting tool accurately and prevent damage to the components during setting.

Setting of the flow rate for a particular set of bores 54/55 is achieved by using the aforesaid setting tool to push the plug radially inwards whilst simultaneously measuring the flow rate of the gas emerging from the bore 57 until the desired setting is reached. The setting plug is a tight, preferably interference, fit in the bore 54 so that, once the correct position is reached, the setting tool may be withdrawn without affecting the plug setting, and the plug will remain in position without the need for further action. The relatively thin wall of the plug, resulting from the formation of the blind bore, means that the walls have a degree of flexure which assists the setting process.

The setting tool accesses the plug via a setting hole 60 linking the chambers 50 and 59. The hole 60 is positioned so as to be in alignment with each bore 54 as the bore set 54/55 is brought into alignment with the bore 57. Thus setting can be carried out with the device configured in the exact way that it would be in service. Setting is carried out with the outlet connector 16 removed so that the hole 60 is exposed. The setting tool comprises a setting rod which extends through the hole 60 into the aligned bore 54, together with means for permitting fine controlled movement of the setting rod in a radially inwards direction to push the plug inwards. Such means can comprise simply a mechanism incorporating a fine thread, or something more sophisticated involving, for example, reduction gearing. Either way, the setting rod is sized so as to locate into the blind bore formed in the setting plug 15. Once the correct setting has been achieved, the setting rod is withdrawn, and the knob 31 rotated to bring the next plug 15 into position for adjustment.

Once setting of all the plug 15 has been completed, the hole 60 is closed by a sealing cover 18 which is retained in position by the outlet connector 16.

Various alternative ways of setting are possible

1) The blind bore at the back of the plug may be threaded to receive a co-operatively-threaded end of the setting rod. In this way, the plug can be withdrawn (i.e. moved radially outwardly) should it be pushed too far during the initial setting.

2) The outside surface of the plug 15 could be threaded to threadedly engage the bore 54, at least the outer part of which would be internally threaded to match. The blind bore in the back of the plug could be made, for example, square to receive a co-operating square end of the setting rod so that rotation of the setting rod would result in rotation of the plug 15 in the threaded bore 54, thereby enabling adjustment to be carried out. With a threaded plug, it might be necessary to apply a thread locking sealant to maintain the setting.

It will also be noted that, should the correct setting be missed, the plug could be pressed further inwards into that part of bore 54 which is inwards of bore 55, in which case the route for the output flow of gas will change slightly to entering bore 55 via an inwards movement along bore 54. In this case, a further opportunity is presented to achieve a correct setting of the plug.

If necessary, a pressure relief valve (not shown) may be provided in the body part 25 to vent to atmosphere excess pressure in the low pressure chamber 50.

The method of flow setting used in the regulator device of the present invention has a number of advantages:

1) The setting adjustments are made from the exterior on the finished assembled regulator device, thus ensuring that minor differences which inevitably occur between different devices are catered for in the setting up. As a result manufacturing tolerances can be less precise than needed when other methods of setting are used.

2) Because the adjustments are made on the finished regulator device, the flows do not need to be known until the last stage of manufacture.

3) The method allows all the flow rates conventionally used for oxygen therapy to be achieved using the same set of component parts.

Other small changes could be made in the described embodiment. For example, the bore set 54/55 could be differently arranged. The bore 55 could extend from the left hand face of the flange 52 right through the flange to the face 56 and the bore 55 could in this case comprise just that part which is radially outward of the bore 55.

Although shown with just a single outlet connector, there are some circumstances where two or even more outlet connections might be provided on the same body. In this case, each such outlet connector could be associated with its own setting hole 60 and sealing cover 18, in the manner described above.

What is claimed is:

1. An adjustable flow regulator device comprising a body, an inlet connector and an outlet connector mounted on said body, regulator means within said body operable to receive gas from said inlet connector and provide a regulated supply, and adjustable flow selector means within said body operable to receive gas from said regulator means and provide an adjustable flow to said outlet connector, said regulator device being characterised in that said flow selector means comprises a passage through which gas flows from said regulator means to said outlet connector and a setting plug adjustably mounted to selectively restrict the passage of gas through said passage, said setting plug having engagement means by which it may be engaged with an externally applied setting tool for adjustment of said plug to obtain the desired gas flow rate through said passage.

2. A device as claimed in claim 1 wherein said setting plug is mounted in a bore and is slidably movable in said bore to provide the adjustable mounting of said setting plug.

3. A device as claimed in claim 2 wherein the setting plug is a tight fit in said bore so that, once set, the plug maintains its position in the bore.

4. A device as claimed in claim 1 wherein said setting plug is mounted in a bore and is a screw threaded fit within said bore to provide the adjustable mounting of said setting plug.

5. A device as claimed in claim 2 wherein the bore is formed in the wall of said passage and wherein the setting plug is movable along said passage so as to protrude out of said passage by an adjustable amount to thereby enable the flow through said passage to be adjusted.

6. A device as claimed in claim 2 wherein said bore emerges at one end at a position where it may be accessed by said setting tool.

7. A device as claimed in claim 6 wherein the body is formed with a setting hole, and wherein said bore is aligned with said setting hole to enable access by the setting tool via the setting hole.

8. A device as claimed in claim 7 wherein the outlet connector is detachable from the body, and said setting hole is positioned underneath the outlet connector, which latter may be detached to enable the setting tool to be used.

9. A device as claimed in any one of the preceding claims wherein the flow selector means further comprises a movable flow selecting member in which is formed a plurality of said passages each having an associated setting plug, means being provided for adjusting the position of said flow selecting member in discrete steps, at each one of which at least one of said passages is in fluid communication with said outlet connector.

10. A device as claimed in claim 9 wherein the flow selecting member is rotatably mounted within said body and is rotated by means of an externally mounted manually adjustable knob.

11. A device as claimed in claim 9 wherein means are provided for locating said flow selecting member at a plurality of predetermined angular spaced positions each corresponding to a position at which said at least one passage is in fluid communication with said outlet connector.

12. A device as claimed in claim 7 wherein said bores are oriented approximately radially with respect to the axis of rotation of the flow selecting member, the arrangement being such that, as the flow selecting member is rotated, a different setting plug can be brought into alignment with the setting hole.

13. A device as claimed in claim 3 wherein the bore is formed in the wall of said passage and wherein the setting plug is movable along said passage so as to protrude out of said passage by an adjustable amount to thereby enable the flow through said passage to be adjusted.

14. A device as claimed in claim 4 wherein the bore is formed in the wall of said passage and wherein the setting plug is movable along said passage so as to protrude out of said passage by an adjustable amount to thereby enable the flow through said passage to be adjusted.

15. A device as claimed in claim 3 wherein said bore emerges at one end at a position where it may be accessed by said setting tool.

16. A device as claimed in claim 4 wherein said bore emerges at one end at a position where it may be accessed by said setting tool.

17. A device as claimed in claim 5 wherein said bore emerges at one end at a position where it may be accessed by said setting tool.

18. A device as claimed in claim 10 wherein means are provided for locating said flow selecting member at a plurality of predetermined angular spaced positions each corresponding to a position at which said at least one passage is in fluid communication with said outlet connector.

19. A device as claimed in claim 10 wherein said bores are oriented approximately radially with respect to the axis of rotation of the flow selecting member, the arrangement being such that, as the flow selecting member is rotated, a different setting plug can be brought into alignment with the setting hole.

20. A device as claimed in claim 11 wherein said bores are oriented approximately radially with respect to the axis of rotation of the flow selecting member, the arrangement being such that, as the flow selecting member is rotated, a different setting plug can be brought into alignment with the setting hole.

* * * * *